US010493161B2

(12) United States Patent
Warashina et al.

(10) Patent No.: US 10,493,161 B2
(45) Date of Patent: Dec. 3, 2019

(54) SOLUTION FOR SPRAY DRYING COMPRISING HYPROMELLOSE ACETATE SUCCINATE AND METHOD FOR PRODUCING SOLID DISPERSION

(71) Applicant: Shin-Etsu Chemical Co., Ltd., Tokyo (JP)

(72) Inventors: Shogo Warashina, Joetsu (JP); Fumie Kusaki, Joetsu (JP); Kazuki Kikuchi, Joetsu (JP); Sakae Obara, Tokyo (JP); Naosuke Maruyama, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/939,510

(22) Filed: Nov. 12, 2015

(65) Prior Publication Data

US 2016/0136283 A1 May 19, 2016

(30) Foreign Application Priority Data

Nov. 18, 2014 (JP) ................................ 2014-233774

(51) Int. Cl.
A61K 47/38 (2006.01)
A61K 47/10 (2017.01)
A61K 47/02 (2006.01)
A61K 31/496 (2006.01)
A61K 9/10 (2006.01)

(52) U.S. Cl.
CPC ............ A61K 47/38 (2013.01); A61K 31/496 (2013.01)

(58) Field of Classification Search
None
See application file for complete search history.

(56) References Cited

U.S. PATENT DOCUMENTS

| 4,226,981 | A | 10/1980 | Onda et al. | |
| 8,343,548 | B2 * | 1/2013 | Kusaki | A61K 9/1623 424/489 |
| 2002/0009494 | A1 | 1/2002 | Curatolo et al. | |
| 2003/0219489 | A1 | 11/2003 | Curatolo et al. | |
| 2008/0038340 | A1 * | 2/2008 | Kusaki | A61K 9/1623 424/464 |
| 2012/0288542 | A1 | 11/2012 | Curatolo et al. | |
| 2012/0292797 | A1 | 11/2012 | Curatolo et al. | |
| 2012/0328679 | A1 | 12/2012 | Curatolo et al. | |
| 2013/0224301 | A1 | 8/2013 | Curatolo et al. | |
| 2015/0024054 | A1 | 1/2015 | Curatolo et al. | |

FOREIGN PATENT DOCUMENTS

| EP | 2810660 A1 | 12/2014 | |
| EP | 3006049 A1 | 4/2016 | |
| JP | S5461282 A | 5/1979 | |
| JP | H11116502 A | 4/1999 | |
| JP | 2004-067606 | 3/2004 | |
| JP | 2008-201009 A | 1/2008 | |
| JP | 2011-516613 A | 5/2011 | |
| JP | 2013116836 | 6/2013 | |
| WO | WO 03043602 A1 * | 5/2003 | ............ A61K 9/146 |
| WO | WO 2005/115330 A2 | 12/2005 | |
| WO | WO 2009/129301 A2 | 10/2009 | |
| WO | WO 2011/159626 A1 | 12/2011 | |
| WO | 2012051035 A1 | 4/2012 | |
| WO | WO 2013154607 A1 * | 10/2013 | ............ A61K 47/38 |
| WO | WO 2014/031422 A1 | 2/2014 | |

OTHER PUBLICATIONS

"Hypromellose Acetate Succinate", Official Monographs, Supplement 1 of Japanese Pharmacopoeia $16^{th}$ Ed. pp. 2426-2428.
European Search Report corresponding to European Application No. 15194983.1 dated Feb. 24, 2016.
"Disintegration Test" of the Japanese Pharamcopoeia, 16th edition, pp. 31-33.
Declaration pursuant to Rule 132 EPC of Shogo Warashina (inventor) on AQOAT of Jan. 6, 2016.
"Methocel Cellulose Ethers" Technical Handbook from The Dow Chemical Company, published Sep. 2002.
Friesen et al. "Hydroxypropyl Methylcellulose Acetate Succinate-Based Spray-Dried Dispersions: An Overview" Molecular Pharmaceutics 5(6):1003-1019 (Dec. 1, 2008).
Communication of a Notice of Opposition corresponding to European Patent Application No. 15194983.1 dated May 18, 2018 (20 pages).
"Test Report" from the Notice of Opposition coressponding to European Patent Application No. 15194983.1 dated May 18, 2018. (2 Pages).
AquaSolve hydroxypropylmethlcellulose acetate succinate, Physical and Chemical properties handbook, 2015, 16 pages.
Turbidity and transmittance of comparative Examples C—H in WO2014/031422 A1, 3 pages.
Communication from the European Patent Office corresponding to EP15194983.1, dated May 3, 2019, 1 page.
Response to communication dated Oct. 12, 2018 corresponding to EP15194983.1, dated Apr. 29, 2019, 13 pages.

* cited by examiner

Primary Examiner — David J Blanchard
Assistant Examiner — Dominic Lazaro
(74) Attorney, Agent, or Firm — Myers Bigel, P.A.

(57) ABSTRACT

There are provided a solution for spray drying having a high transmittance and markedly reduced generation of undissolved matter; and a method for producing a solid dispersion by using the solution for spray drying so that clogging with the undissolved matter is reduced and dissolution is improved. More specifically, there is provided a solution for spray drying comprising hypromellose acetate succinate (HPMCAS) having a hydroxypropoxy molar substitution of 0.40 or more, a solvent, and a drug. There is also provided a method for producing a solid dispersion comprising the step of removing the solvent from the spray drying solution.

8 Claims, No Drawings

SOLUTION FOR SPRAY DRYING COMPRISING HYPROMELLOSE ACETATE SUCCINATE AND METHOD FOR PRODUCING SOLID DISPERSION

RELATED APPLICATION

This application claims priority from Japanese Patent Application No. 2014-233774, filed Nov. 18, 2014, the disclosure of which is incorporated by reference herein in its entirety.

FIELD AND BACKGROUND OF THE INVENTION

The present invention relates to a solution for spray drying comprising hypromellose acetate succinate and a method for producing a solid dispersion.

A method for producing a solid dispersion comprising the steps of: dissolving a mixed solution of a drug and a polymer in a solvent, and removing the solvent for precipitation, has recently attracted attentions as a pharmaceutical preparation technique.

For example, a solid dispersion obtained by spray-drying a poorly water-soluble drug and a polymer has improved bioavailability because solubility of the drug apparently shows a marked increase due to molecular dispersion of the drug in the polymer carrier where the drug is in amorphous form.

One of the polymers to be used for such a solid dispersion is a hypromellose acetate succinate (hereinafter also referred to as "HPMCAS"), which is a polymer obtained by introducing four substituents in total. Two substituents, a methoxy group ($-OCH_3$) and a hydroxypropoxy group ($-OC_3H_6OH$), are introduced into a cellulose skeleton to form an ether structure and the other two substituents, an acetyl group ($-COCH_3$) and a succinyl group ($-COC_2H_4COOH$) are introduced to form an ester structure.

The content of each substituent of HPMCAS is listed in the Japanese Pharmacopoeia 16th Edition ("Hypromellose Acetate Succinate", Official Monographs, Supplement I of the Japanese Pharmacopoeia 16th Edition) and is shown below.

TABLE 1

| | content (% by weight) | molar substitution (MS)*1 |
|---|---|---|
| methoxy group | 12.0~28.0 | 0.73~2.83 |
| hydroxypropoxy group | 4.0~23.0 | 0.10~1.90 |
| acetyl group | 2.0~16.0 | 0.09~2.30 |
| succinyl group | 4.0~28.0 | 0.08~1.78 |

*1 The molar substitution means an average mole of each introduced substituent per glucose ring unit of cellulose.

As a solid dispersion comprising HPMCAS, for example, a spray-dried solid dispersion comprising a poorly soluble drug and HPMCAS (commercially available AS having a molar substitution of from 0.16 to 0.35) is known (see JP 11-116502A).

In addition, a method for producing a preparation comprising the step of spray-drying posaconazole, which is a poorly water-soluble drug, and HPMCAS (commercially available AS-MF and AS-MG having a molar substitution of from 0.15 to 0.34) is proposed (see JP 2011-516613T which is the Japanese phase publication of WO 2009/129301A). A method for producing a preparation comprising the step of spray-drying itraconazole, which is a poorly water-soluble drug, and HPMCAS (commercially available AS-HG having a molar substitution of from 0.15 to 0.34) is also proposed (see JP 2004-067606A).

Further, a method of spray-drying a solid dispersion comprising a poorly water-soluble drug and HPMCAS having a hydroxypropoxy molar substitution of 0.25, a succinyl molar substitution of 0.02 or more, an acetyl molar substitution of 0.65 or more, and a total molar substitution of acetyl and succinyl groups of 0.85 or more is further proposed (see JP 2008-501009T, which is the Japanese phase publication of WO 2005/115330A). A method for spray-drying a solid dispersion comprising HPMCAS having a hydroxypropoxy molar substitution of 0.21 or less, a methoxyl molar substitution of 1.45 or less and a total molar substitution of acetyl and succinyl groups of 1.25 or more is also proposed (see WO2011159626A).

HPMCAS having a hydroxypropoxy molar substitution of 0.26 or less, a weight-average molecular weight Mw of from 80000 to 350000 Da, turbidity of 41 NTU or less as a 1.5% by weight solution thereof in acetone, and a viscosity of 4.0 mPa·s or less as a 2.0% by weight alkali (0.43% by weight) solution thereof (see WO2014/031422A).

SUMMARY OF THE INVENTION

Any solvent capable of dissolving both a drug and a polymer is used for production of a solid dispersion. Each HPMCAS described in JP 11-116502A, JP 2011-516613T, JP 2004-067606A, JP 2008-501009T and WO2011/159626A has low solubility in a solvent so that undissolved or half-dissolved matter is present in the solution. In general, a solution having both a drug and HPMCAS dissolved therein is filtered for removal of undissolved matter before coating or spray-drying. However, when an amount of the undissolved matter is excessively large, the filter is clogged. Even when the filter is not used, a nozzle used for spray-drying may be clogged. According to WO2014/031422A, when HPMCAS as a 1.5% by weight solution thereof in acetone has too low turbidity (not more than 10 NTU), it is not suited for long term use because of reduction in molecular weight MW.

With the foregoing in view, the present invention has been made. According to the invention, a solution for spray drying which has high transmittance and markedly reduces generation of undissolved matter can be provided. In addition, the production of a solid dispersion by using the solution for spray drying can reduce clogging with undissolved matter and improve dissolution.

The present inventors have carried out an extensive investigation to solve the above problems. As a result, it has been found that HPMCAS having improved solubility in a solvent and thereby having high transmittance can be obtained by selecting the specific range of the hydroxypropoxy molar substitution with respect to the four kinds of substituents of the HPMCAS, leading to completion of the invention.

In one aspect of the invention, there is provided a solution for spray drying comprising hypromellose acetate succinate (HPMCAS) having a hydroxypropoxy molar substitution of 0.40 or more, a solvent, and a drug. In another aspect of the invention, there is provided a method for producing a solid dispersion comprising the step of removing the solvent from the solution for spray drying.

According to the invention, higher solubility of HPMCAS in a solvent compared with the conventional one results in high transmittance and reduction of clogging during removal of undissolved matter through a filter.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

According to the invention, the HPMCAS has a hydroxypropoxy molar substitution of 0.40 or more, preferably from 0.40 to 1.50, more preferably from 0.40 to 1.0, still more preferably from 0.40 to 0.90. When the hydroxypropoxy molar substitution is less than 0.40, undissolved or half dissolved matter is present in the solution of HPMCAS in a solvent so that it may clog a filter or a nozzle.

The content of each substituent of the HPMCAS including a hydroxypropoxy group can be analyzed by a method described in "Hypromellose Acetate Succinate", Official Monographs, Supplement I of the Japanese Pharmacopoeia 16th Edition.

With regard to the solubility of the HPMCAS in a solvent, the transmittance of 10% by weight solution of HPMCAS in acetone, which is a solvent to be used generally for production of a solid dispersion, is preferably 50% or more, more preferably 60% or more, still more preferably 70% or more, particularly preferably 80% or more.

The transmittance of a solution of the HPMCAS in acetone is measured as follows. After addition of 10 g of HPMCAS to 90 g of acetone at 20° C., the resulting mixture is agitated for 3 hours with an agitating blade at a speed of about 400 rpm to prepare a 10% by weight solution of HPMCAS in acetone. The transmittance of the resulting solution is measured using a transmittance-measuring apparatus (photoelectric colorimeter "PC-50", product of Kotaki Manufacturing Co.) equipped with a 720-nm filter and a 20-mm cell. Distilled water is used as control and the apparatus is adjusted to make the transmittance of the distilled water to be 100%.

The molar substitution of the methoxy group, which is one of the substituents other than the hydroxypropoxy group in the HPMCAS, is not particularly limited. The molar substitution of the methoxy group is preferably from 0.70 to 2.90, more preferably from 1.00 to 2.40, still more preferably from 1.4 to 1.9.

The molar substitution of the acetyl group in the HPMCAS is also not particularly limited. The molar substitution of the acetyl group is preferably from 0.10 to 2.50, more preferably from 0.10 to 1.00, still more preferably from 0.40 to 0.96.

The molar substitution of the succinyl group in the HPMCAS is not particularly limited. The molar substitution of the succinyl group is preferably from 0.10 to 2.50, more preferably from Q.10 to 1.00, still more preferably from 0.10 to 0.60.

The viscosity at 20° C. of a dilute (0.1 mol/L) aqueous sodium hydroxide solution containing 2% by weight of the HPMCAS is preferably from 1.1 to 20 mPa·s, more preferably from 1.5 to 3.6 mPa·s. When the viscosity is less than 1.1 mPa·s, the mist generated during spray may become too fine to be collected. When the viscosity is more than 20 mPa·s, the increased viscosity brings marked reduction in productivity during spray drying. The viscosity can be measured by the method described in General Tests of HPMCAS in the Japanese Pharmacopoeia 16th Edition.

The HPMCAS can be produced using the method described in, for example, JP 54-061282A. The method comprises the steps of dissolving, in glacial acetic acid, hypromellose (another name: hydroxypropylmethyl cellulose which may hereinafter be also referred to as "HPMC") as a starting material; adding acetic anhydride and succinic anhydride as esterifying agents in the presence of sodium acetate as a reaction catalyst for a thermal reaction; adding a large amount of water to the reaction mixture to precipitate the HPMCAS after completion of the reaction; washing the resulting precipitate with water; and then drying. If a HPMC having a hydroxypropoxy molar substitution of 0.40 or more is used, then the produced HPMCAS will have a hydroxypropoxy molar substitution of 0.40 or more.

A drug is not particularly limited insofar as it is an orally administrable. The drug may be used singly or as a mixture of two or more. Examples of the drug include drugs for the central nervous system, drugs for the circulatory system, drugs for the respiratory system, drugs for the digestive system, antibiotics, antitussives/expectorants, antihistamines, analgesic antipyretic anti-inflammatory drugs, diuretics, autonomic drugs, antimalarial drugs, antidiarrheal agents, psychotropic drugs, and vitamins and derivatives thereof.

Examples of the drugs for the central nervous system include diazepam, idebenone, aspirin, ibuprofen, paracetamol, naproxen, piroxicam, dichlofenac, indomethacin, sulindac, lorazepam, nitrazepam, phenytoin, acetaminophen, ethenzamide, ketoprofen, and chlordiazepoxide.

Examples of the drugs for the circulatory system include molsidomine, vinpocetine, propranolol, methyldopa, dipyridamole, furosemide, triamterene, nifedipine, atenolol, spironolactone, metoprolol, pindolol, captopril, isosorbide dinitrate, isosorbide mononitrate, delapril hydrochloride, meclofenoxate hydrochloride, diltiazem hydrochloride, etilefrine hydrochloride, digitoxin, propranolol hydrochloride, and alprenolol hydrochloride.

Examples of the drugs for the respiratory system include amlexanox, dextromethorphan, theophilline, pseudo-ephedrine, salbutamol, and guaiphenesin.

Examples of the drugs for the digestive system include benzimidazole-based drugs having anti-ulcer action such as 2-[[3-methyl-4-(2,2,2-trifluoroethoxy)-2-pyridyl]methylsulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicylic acid.

Examples of the antibiotics include talampicillin hydrochloride, bacampicillin hydrochloride, cephaclor, and erythromycin.

Examples of the antitussives/expectorants include noscapine hydrochloride, carbetapentane citrate, dextromethorphan hydrobromide, isoaminile citrate, and dimemorfan phosphate.

Examples of the antihistamines include chlorpheniramine maleate, diphenhydramine hydrochloride, and promethazine hydrochloride.

Examples of the analgesic, antipyretic, and anti-inflammatory drugs include ibuprofen, diclofenac sodium, flufenamic acid, sulpyrine, aspirin, and ketoprofen.

Examples of the diuretics include caffeine.

Examples of the autonomic drugs include dihydrocodeine phosphate, dl-methylephedrine hydrochloride, propranolol hydrochloride, atropine sulfate, acetylcholine chloride, and neostigmine.

Examples of the antimalarial drugs include quinine hydrochloride.

Examples of the antidiarrheal agents include loperamide hydrochloride.

Examples of the psychotropic drugs include chlorpromazine.

Examples of the vitamins and derivatives thereof include Vitamin A, Vitamin B1, fursultiamine, Vitamin B2, Vitamin B6, Vitamin B12, Vitamin C, Vitamin D, Vitamin E, Vitamin K, calcium pantothenate, and tranexamic acid.

In particular, by using the HPMCAS as a carrier for a poorly water-soluble drug in a solid dispersion in accordance with the invention, the poorly water-soluble drug can have improved solubility. The term "poorly water-soluble drug" as used herein means a drug categorized as "slightly soluble", "very slightly soluble", or "practically insoluble, or insoluble" described in the Japanese Pharmacopoeia 16th Edition. The term "slightly soluble" means that the amount of water required for dissolution within 30 minutes at 20±5° C. is 100 mL or more but less than 1000 mL when 1 g or 1 mL of a pharmaceutical in solid form is placed in a beaker, the water is poured in the beaker, and the resulting mixture is vigorously shaken for 30 seconds each time at 5-minute intervals. The term "very slightly soluble" means that the amount of water required for dissolution within 30 minutes at 20±5° C. is 1000 mL or more but less than 10000 mL when measured in the same manner. The term "practically insoluble, or insoluble" means that the amount of water required for dissolution within 30 minutes at 20±5° C. is 10000 mL and more when measured in the same manner.

In the above-mentioned pharmaceutical test, the dissolution of a poorly water-soluble drug means that it dissolves or becomes miscible in a solvent and fibers or the like are not observed or if any, only a trace amount of them is observed.

Specific examples of the poorly water-soluble drug include azole-based compounds such as itraconazole, ketoconazole, fluconazole and miconazole; dihydropyridine-based compounds such as nifedipine, nitrendipine, amlodipine, nicardipine, nilvadipine, felodipine and efonidipine; propionic acid-based compounds such as ibuprofen, ketoprofen and naproxen; and indoleacetic acid-based compounds such as indomethacin and acemetacin. Additional examples include griseofulvin, phenytoin, carbamazepine and dipypridamole.

A weight ratio of HPMCAS to a drug is not particularly limited. The weight ratio of HPMCAS to a drug is preferably from 1:0.01 to 1:100, more preferably from 1:0.1 to 1:10, still more preferably from 1:0.2 to 1:5 from the standpoint of storage stability in amorphized form.

According to the invention, a solvent for the solution for spray drying is an arbitrary solvent capable of dissolving both the drug and the HPMCAS therein. Examples of the solvent preferably include water, acetone, methanol, ethanol, isopropanol, methyl acetate, ethyl acetate, tetrahydrofuran, and dichloromethane. The solvent may be used singly or in combination of two or more. When the solution for spray drying contains a water-miscible solvent, water may be added to the solution.

An optional various additive ordinarily used in this field such as an excipient, a binder, a disintegrant, a lubricant and an agglomeration preventive may be added to the solution for spray drying, and then the resulting mixture may be used for formation of an oral solid preparation such as a tablet, a granule, a fine granule and a capsule; and an oral film preparation.

Examples of the excipient include sugars such as sucrose, lactose, mannitol, and glucose; starch; and crystalline cellulose.

Examples of the binder include polyvinyl alcohol, polyacrylic acid, polyvinylpyrrolidone, hydroxyethyl cellulose, hydroxypropylmethyl cellulose, hydroxypropyl cellulose, macrogols, gum Arabic, gelatin, and starch.

Examples of the disintegrant include low-substituted hydroxypropyl cellulose, carmellose or salts thereof, croscarmellose sodium, carboxymethyl starch sodium, crospovidone, crystalline cellulose, and crystalline cellulose carmellose sodium.

Examples of the lubricant and the agglomeration preventive include talc, magnesium stearate, calcium stearate, colloidal silica, stearic acid, waxes, hydrogenated oil, polyethylene glycols, and sodium benzoate.

The oral solid preparation thus obtained may be film-coated with a water-soluble coating agent such as methyl cellulose or hypromellose, or may be coated with an enteric coating agent such as hypromellose acetate succinate, hypromellose phthalate, or methacrylate acrylate copolymer.

Next, a method for producing a solid dispersion will be described.

More specifically, the solid dispersion is produced by the method comprising the step of removing a solvent or precipitating a solid dispersion from the solution for spray drying comprising HPMCAS having a hydroxypropoxy molar substitution of 0.40 or more and enabling a 10% by weight solution of the HPMCAS in acetone to have transmittance of preferably 50% or more, a solvent, and at least one drug. The solution for spray drying is preferably a uniform solution having a drug and HPMCAS dissolved therein as uniformly as possibly. Examples of the method for removing the solvent include evaporation to dryness, and spray drying. In the present invention, the spray drying is used because the spray drying allows mass production and easy control of powder properties such as a particle size and a bulk density.

The term "spray drying" broadly means a method comprising the steps of breaking down or spraying a solution containing a poorly soluble drug into small droplets and removing the solvent from the droplets rapidly through evaporation. Driving force for removing the solvent can be obtained by lowering a partial pressure of the solution lower than the vapor pressure of the solvent at an ordinarily employed drying temperature of the droplets. For example, a method of mixing the droplets with a high temperature drying gas, or a method of keeping a pressure in a solvent-removing apparatus reduced may be preferably applied.

The solution for spray drying comprising the drug and the HPMCAS together with a solvent can be spray-dried using a variety of nozzle mechanism. For example, various types of nozzles can be used. For example, a two-fluid nozzle, a fountain type nozzle, a flat fan-shaped nozzle, a pressure nozzle, or a rotary atomizer can be preferably used.

The solution for spray drying can be fed at wide ranges of flow rate and temperature. When a pressure is applied during spraying, the spray can be carried out at a wide range of pressure. In general, as the specific surface area of droplets increases, a solvent evaporation rate increases. At the time of release from the nozzle, the droplets have a size of preferably less than 500 μm, more preferably less than 400 μm, still more preferably from 5 to 200 μm. The flow rate, temperature and pressure enabling the droplets to have such a size are preferably used. After spraying, the solution solidifies rapidly.

The solution for spray drying solidifies rapidly after sprayed, and becomes a solid dispersion. In general, the solid dispersion thus obtained by solidification remains in a spray drying chamber for about 5 to 60 seconds for which the solvent is removed from the solid powder. As the spray drying temperature, an inlet temperature is preferably from about 20° C. to 150° C. and an outlet temperature is preferably from 0° C. to 85° C.

The solvent content remaining in the solid dispersion is preferably as small as possible. The small solvent content suppresses motility of a drug molecule in the amorphous solid dispersion and increases the stability. When further removal of the remaining solvent is required, the secondary drying can be carried out. Examples of the preferable secondary drying method include tray drying, fluidized bed drying, belt drying, and microwave drying.

The invention will hereinafter be described specifically by Examples and Comparative Examples. However, it should not be construed that the invention is limited to or by them.

EXAMPLES

<Synthesis of HPMCAS-1>

In a 50-L kneader, 12 kg of glacial acetic acid was weighed, and 6 kg of hypromellose (HPMC) having a hydroxypropoxy molar substitution of 0.86 and a methoxy molar substitution of 1.59 was added thereto and dissolved therein. Further, 4.0 kg of acetic anhydride, 2.2 kg of succinic anhydride and 4.8 kg of sodium acetate were added thereto and allowed to react at 85° C. for 5 hours. After addition of purified water (6.7 kg) thereto and stirring, purified water was further added to the reaction mixture to precipitate HPMCAS in granular form. Crude HPMCAS was collected by filtration. The crude HPMCAS was washed with purified water, dried, and then filtered through a 10-mesh sieve (opening size: 1700 μm) to obtain HPMCAS-1 having final water content of 1.2% by weight.

The content of each of the substituents of the produced HPMCAS-1 was measured in accordance with the method described in the Japanese Pharmacopoeia 16th Edition, Supplement I. As a result, HPMCAS-1 was found to have hydroxypropoxy content of 20.6% by weight (molar substitution of 0.86), methoxy content of 15.8% by weight (molar substitution of 1.59), acetyl content of 6.8% by weight (molar substitution of 0.49), and succinyl content of 18.7% by weight (molar substitution of 0.58).

<Synthesis of HPMCAS-2 to 9>

By using a starting material HPMC different in the content of each substituent, and appropriately changing the amounts of acetic anhydride and succinic anhydride, various HPMCAS-2 to 9 shown in Table 2 were obtained in the same manner as in Synthesis of HPMCAS-1.

TABLE 2

| | molar substitution | | | |
|---|---|---|---|---|
| | hydroxypropoxy | methoxy | acetyl | succinyl |
| HPMCAS-1 | 0.86 | 1.59 | 0.49 | 0.58 |
| HPMCAS-2 | 0.84 | 1.58 | 0.80 | 0.22 |
| HPMCAS-3 | 0.63 | 1.83 | 0.54 | 0.28 |
| HPMCAS-4 | 0.62 | 1.85 | 0.68 | 0.23 |
| HPMCAS-5 | 0.59 | 1.81 | 0.73 | 0.18 |
| HPMCAS-6 | 0.58 | 1.57 | 0.96 | 0.22 |
| HPMCAS-7 | 0.45 | 1.91 | 0.62 | 0.26 |
| HPMCAS-8 | 0.26 | 1.64 | 0.55 | 0.38 |
| HPMCAS-9 | 0.25 | 1.89 | 0.54 | 0.27 |

<Measurement of Transmittance of HPMCAS>

Transmittance of HPMCAS-1 to 9 was measured. More specifically, 10 g of each HPMCAS was added to 90 g of acetone at 20° C. and then stirred at a speed of about 400 rpm with an agitation blade for 3 hours to prepare a 10% by weight solution of HPMCAS in acetone. The transmittance of the solution was measured using a transmittance-measuring apparatus (photoelectric colorimeter "PC-50", product of Kotaki Manufacturing Co.) equipped with a 720-nm filter and a 20-mm cell. Distilled water was used as control and the apparatus was adjusted to make the transmittance of the distilled water to be 100%.

TABLE 3

| HPMCAS | transmittance (%) |
|---|---|
| HPMCAS-1 | 91.2 |
| HPMCAS-2 | 94.8 |
| HPMCAS-3 | 89.2 |
| HPMCAS-4 | 93.3 |
| HPMCAS-5 | 90.8 |
| HPMCAS-6 | 93.1 |
| HPMCAS-7 | 92.2 |
| HPMCAS-8 | 5.3 |
| HPMCAS-9 | 6.1 |

Each of HPMCAS-1 to HPMCAS-7 having a hydroxypropoxy molar substitution of 0.40 or more had a transmittance as high as 89.2% or more, each of HPMCAS-8 and HPMCAS-9 having a hydroxypropoxy molar substitution of less than 0.4 had a transmittance as low as 6.1% or less and were found to be visually turbid. Such a high transmittance is presumed to occur because an increase in hydroxypropoxy group has caused marked enhancement of solubility in a solvent.

Examples 1 to 7 and Comparative Examples 1 and 2

A solution for spray drying was prepared by dissolving 1 g of ketoconazole as a poorly water-soluble drug, and 1 g of each HPMCAS in a mixed solution of dichloromethane and ethanol at the weight ratio of 1:1. The resulting solution for spray drying was spray dried using a spray dryer ("B-290", product of Nippon Mich K.K.) at an intake air temperature of 120° C., an exhaust air temperature of 75° C., a liquid feed rate of 3 g/min, and an internal pressure of 3 MPa (30 bar). The dried solid matter was collected and subjected to the dissolution test described in the Japanese Pharmacopoeia 16th Edition.

A dissolution (% by weight) of ketoconazole from 180 mg of the powder (equivalent to 90 mg of ketoconazole) was measured using 900 mL of the 2nd fluid (pH 6.8) for Disintegration Test of the Japanese Pharmacopoeia 16th Edition and a Japanese Pharmacopoeia dissolution tester ("NTR-6100A", product of Toyama Sangyo Co., Ltd.) at a paddle rotation speed of 100 rpm. The ketoconazole was quantitatively determined by measuring UV absorbance (wavelength of 225 nm and light path length of 10 mm) and determining the dissolution amount of ketoconazole based on an absorbance conversion line drawn in advance at known concentrations. The results are shown in Table 4.

TABLE 4

| | | dissolution of ketoconazole (% by weight) *1 | | | |
|---|---|---|---|---|---|
| | HPMCAS | 0 mins | 10 mins | 30 mins | 60 mins |
| Example 1 | HPMCAS-1 | 0 | 42.2 | 56.4 | 55.4 |
| Example 2 | HPMCAS-2 | 0 | 33.0 | 54.9 | 62.5 |
| Example 3 | HPMCAS-3 | 0 | 98.5 | 90.9 | 68.6 |
| Example 4 | HPMCAS-4 | 0 | 53.3 | 73.7 | 79.2 |
| Example 5 | HPMCAS-5 | 0 | 32.0 | 53.3 | 61.0 |
| Example 6 | HPMCAS-6 | 0 | 30.5 | 47.7 | 53.3 |
| Example 7 | HPMCAS-7 | 0 | 89.9 | 90.9 | 80.3 |
| Comp. Ex. 1 | HPMCAS-8 | 0 | 48.3 | 59.9 | 42.7 |
| Comp. Ex. 2 | HPMCAS-9 | 0 | 82.3 | 49.8 | 30.0 |

*1 Dissolution of ketoconazole at each dissolution time (minutes) is shown.

Compared with each powder produced in Comparative Examples 1 and 2 containing HPMCAS having a hydroxypropoxy molar substitution of less than 0.4, each powder produced in Examples 1 to 7 containing HPMAS having a hydroxypropoxy molar substitution of 0.4 or more was found to keep a dissolution percentage as high as 53.3% by weight or more even after 60 minutes from the start of the test. Initial dissolution improvement and long-lasting dissolution are presumed to occur not only because an increase in hydroxypropoxy molar substitution has enhanced recrystallization inhibiting ability but also because an increase in hydroxypropoxy molar substitution has enhanced the solubility of HPMCAS in the solvent in the solution for spray drying, thereby allowing the HPMCAS to be uniformly mixed with the dug in the solvent for formation of a uniform solid dispersion.

As a result of analyses of X-ray diffraction images of the powders, no crystal peak of ketoconazole was found in the X-ray diffraction images and a dissolution of ketoconazole was markedly high. This suggests that a solid dispersion formed from the solution for spray drying has ketoconazole being in amorphous form and dispersed in HPMCAS.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

That which is claimed:

1. A solution for spray drying comprising hypromellose acetate succinate having a hydroxypropoxy molar substitution of 0.40 to 1.50, a solvent, and a drug, wherein the transmittance of a 10% by weight solution of the hypromellose acetate succinate in solvent is 50% or more.

2. The solution for spray drying according to claim 1, wherein the drug is a poorly water-soluble drug.

3. The solution for spray drying according to claim 1, wherein the solvent is one or more selected from the group consisting of water, acetone, methanol, ethanol, isopropanol, methyl acetate, ethyl acetate, tetrahydrofuran, and dichloromethane.

4. The solution for spray drying according to claim 1, wherein the hypromellose acetate succinate has a methoxy molar substitution of 0.70 to 2.90.

5. A method for producing a solid dispersion comprising the steps of:
providing the solution for spray drying as claimed in claim 1,
spray drying the solution for spray drying to remove the solvent therefrom.

6. The method for producing a solid dispersion according to claim 5, wherein the drug is a poorly water-soluble drug.

7. The method for producing a solid dispersion according to claim 5, wherein the solvent is one or more selected from the group consisting of water, acetone, methanol, ethanol, isopropanol, methyl acetate, ethyl acetate, tetrahydrofuran, and dichloromethane.

8. The method for producing a solid dispersion according to claim 5, wherein the hypromellose acetate succinate has a methoxy molar substitution of 0.70 to 2.90.

* * * * *

UNITED STATES PATENT AND TRADEMARK OFFICE
CERTIFICATE OF CORRECTION

PATENT NO. : 10,493,161 B2  
APPLICATION NO. : 14/939510  
DATED : December 3, 2019  
INVENTOR(S) : Warashina et al.

Page 1 of 1

It is certified that error appears in the above-identified patent and that said Letters Patent is hereby corrected as shown below:

On the Title Page

Item (56) References Cited, FOREIGN PATENT DOCUMENTS, Column 2, Line 3:  
Please correct "JP 2008-201009 A" to read -- JP 2008-501009 A --

In the Specification

Column 4, Line 7:  
Please correct "Q.10" to read -- 0.10 --

Signed and Sealed this  
Fifth Day of May, 2020

Andrei Iancu  
*Director of the United States Patent and Trademark Office*